United States Patent [19]

Klaveness et al.

[11] Patent Number: 4,985,233
[45] Date of Patent: Jan. 15, 1991

[54] A DIAGNOSTIC AGENT CONTAINING A NON-RADIOACTIVE PARAMAGNETIC METAL SPECIES IN A MACROMOLECULAR CARRIER

[75] Inventors: Jo Klaveness; Trond Jacobsen, both of Oslo, Norway; Bernt J. Lindberg, Storvreta, Sweden

[73] Assignee: Nycomed /AS, Olso, Norway

[21] Appl. No.: 793,899

[22] Filed: Nov. 1, 1985

[30] Foreign Application Priority Data

Nov. 1, 1984 [SE] Sweden ................................ 8405500
Nov. 1, 1984 [SE] Sweden ................................ 8405501

[51] Int. Cl.$^5$ ............................................ A61K 49/00
[52] U.S. Cl. ........................................ 424/9; 436/173; 436/806; 128/654; 128/653 R; 128/653 A; 534/15; 536/17.1; 536/51; 536/101; 536/112; 536/113; 536/121
[58] Field of Search ..................... 424/9; 436/173, 806; 128/653, 654; 534/15; 536/17.1, 51, 101, 112, 113, 121

[56] References Cited

U.S. PATENT DOCUMENTS

| | | | |
|---|---|---|---|
| 2,862,920 | 12/1958 | Berger et al. ...................... | 536/113 |
| 3,495,954 | 3/1967 | Grimes et al. ..................... | 536/121 |
| 3,563,978 | 2/1971 | Ochs .................................... | 536/121 |
| 3,928,581 | 12/1975 | Dahlberg et al. .................. | 536/121 |
| 4,370,476 | 1/1983 | Usher et al. ........................ | 536/113 |
| 4,423,158 | 12/1983 | Porath ................................. | 521/32 |
| 4,452,773 | 6/1984 | Molday ............................... | 436/529 |
| 4,615,879 | 10/1986 | Runge et al. ....................... | 424/9 |
| 4,647,447 | 3/1987 | Gries et al. ......................... | 424/2 X |
| 4,675,173 | 6/1987 | Widder ............................... | 436/173 |
| 4,731,239 | 3/1988 | Gordon ............................... | 424/9 |
| 4,822,594 | 4/1989 | Gibby .................................. | 424/9 |

FOREIGN PATENT DOCUMENTS

| | | |
|---|---|---|
| 8633082 | 1/1983 | Australia . |
| 0135125 | 8/1984 | European Pat. Off. . |
| 0136812 | 8/1984 | European Pat. Off. . |
| 0160552 | 4/1985 | European Pat. Off. . |
| 84/00020 | 1/1984 | PCT Int'l Appl. . |
| WO85/05554 | 12/1985 | PCT Int'l Appl. . |
| 78/00001 | 6/1978 | Sweden . |
| 84/00437 | 12/1984 | Sweden . |
| 2137612A | 1/1984 | United Kingdom . |
| 85/00234 | 5/1985 | United Kingdom . |

OTHER PUBLICATIONS

*Concise Encyclopedia of Chemical Technology*, pp. 55–56 (1988)
Structure of An Iron–Dextran Complex, J. Pharm. Pharmac. 1972, 24, pp. 513–517, Cox et al.
The Merck Index, 9th Ed. 1976, p. 2911.
High Resolution NMR, Acadm. Press 1980, Becker, pp. 48–51.
Work In Progress: Potential Oral and Intravenous Paramagnetic NMR Contrast Agents, RADIOLOGY, vol. 147, No. 3, Jul.'83, Runge et al., pp. 789–791.
Desreux, Inorg. Chem., vol 19 (1980), pp. 1319–1324.

*Primary Examiner*—Richard L. Raymond
*Attorney, Agent, or Firm*—Bacon & Thomas

[57] ABSTRACT

A paramagnetic metal species-containing diagnostic agent is disclosed which comprises a non-radioactive paramagnetic metal species and, as a carrier therefor, a physiologically tolerable, water-insoluble, hydroxyl group-containing, particulate macromolecular product consisting essentially of at least one polymeric or polymerized carbohydrate or polymerized sugar alcohol or derivative thereof.

22 Claims, No Drawings

A DIAGNOSTIC AGENT CONTAINING A NON-RADIOACTIVE PARAMAGNETIC METAL SPECIES IN A MACROMOLECULAR CARRIER

The present invention relates to a diagnostic agent containing a paramagnetic metal species, which diagnostic agent is for use in diagnosis based on NMR (Nuclear Magnetic Resonance) and ultrasound signals which are transformed into pictures over the examined area of a body of a human or non-human animal.

In NMR imaging the signal intensity (or contrast in the NMR picture) depends strongly on the nuclear density, the relaxation times and the parameters of the instrument (pulse sequence, frequency, etc.).

There are numerous methods of enhancing the contrast in NMR imaging, but many of these methods, such as manipulation of temperature, viscosity or other physical parameters, are not clinically usable. The use of paramagnetic compounds, however, which at small concentrations reduce the spin-lattice relaxation time ($T_1$) and at higher concentrations reduce the spin-spin relaxation time ($T_2$), appeared to be a favourable way to improve the contrast.

Diagnostic agents for use in NMR imaging and NMR in vivo spectroscopy have been reviewed by many authors, vide e.g. Sem. Nucl. Med., 13 (1983) 364, Radiology 147 (1983) 781 and J. Nucl. Med., 25 (1984) 506. These references primarily disclose inorganic paramagnetic salts but simple organic complexes are also mentioned.

Paramagnetic complexes for use in NMR diagnosis are also disclosed by EP-A-71564 and DE-A-34 01 052. These references describe chelate complexes formed from paramagnetic metal ions and various complex-forming agents containing organic nitrogen, phosphorus, oxygen and/or sulphur, primarily aminopolycarboxylic acids, e.g. ethylenediaminetetraacetic acid (EDTA) and diethylenetriaminepentaacetic acid (DTPA).

The toxicity of such chelate complexes is lower than that of contrast agents based on non-chelated paramagnetic metal ions, such as $Mn^{2+}$ and $Gd^{3+}$. However, the efficiency of such complexes of comparatively low molecular size is not improved considerably over that of inorganic paramagnetic salts.

Complexes comprising a paramagnetic metal species and a protein, such as an antibody, are disclosed by DE-A-3401052 and paramagnetic complexes bound to certain biomolecules such as proteins, hormones etc are also discussed in EP-A-71564. In comparison with the above mentioned simple organic complexes of lower molecular size such complexes exhibit improved efficiency. However, the use of proteins is accompanied by several disadvantages.

Proteins are substances of very complicated structure and generally possess limited stability and applicability. Thus they are difficult to formulate into solutions and they should not be subjected to treatment by heat, which means that diagnostic agents containing proteins cannot be sterilized by the application of heat. The shelf life of such diagnostic agents will be limited and the proteins often exert an effect of their own which is not wanted in connection with the diagnostic investigation. The possibilities of choosing materials for different diagnostic purposes or materials with a desired way of excretion and a desired rate of elimination from the body of an animal (human or non-human) are also limited. Similar problems arise with the other biomolecules suggested as paramagnetic metal carriers in EP-A-71564.

It is an object of the present invention to provide a new diagnostic agent containing a paramagnetic metal species, which diagnostic agent is more efficient than known low-molecular weight paramagnetic metal chelate containing diagnostic agents and than known water insoluble paramagnetic metal containing particulate diagnostic agents.

We have now found that good levels of efficiency may be achieved by using as a carrier for the paramagnetic metal species in a diagnostic agent a water insoluble macromolecular material comprising a polymeric or polymerized carbohydrate or a polymerized sugar alcohol or derivative thereof.

According to one aspect of the invention we therefore provide a diagnostic agent containing a non-radioactive paramagnetic metal species, characterized in that said agent comprises a physiologically tolerable, water-insoluble, hydroxyl group-containing macromolecular product in particulate form, said macromolecular product comprising at least one material selected from the group comprising polymeric and polymerized carbohydrates and polymerized sugar alcohols and derivatives thereof, and said macromolecular product serving as a carrier for at least one non-radioactive paramagnetic metal species.

The paramagnetic metal species in the diagnostic agent of the invention may be chemically bound to the macromolecular carrier or alternatively may be present in solid or liquid inclusions within the carrier product. The carrier product particularly preferably comprises a material cross-linked to form a three-dimensional network swellable but insoluble in water. In the case of such swellable carrier products where the swellable products exhibit cavities these may conveniently be at least partially filled with at least one paramagnetic metal species-containing substance which is insoluble or only sparingly soluble in water.

The present invention thus provides diagnostic agents containing a paramagnetic metal species, which diagnostic agents are based on well documented polymer compounds of simple structures and which, for instance, can easily be formulated, have a good shelf life and are well tolerated.

The present invention thus also provides diagnostic agents containing a paramagnetic metal species, the distribution and elimination of which diagnostic agents within the body under investigation can easily be varied by the use of polymers of different structures.

Hereinafter that part of the macromolecular product which comprises the polymeric or polymerized carbohydrate or polymerized sugar alcohol or derivative thereof will be referred to as "the basic molecule of the macromolecular product". The term "polymeric carbohydrate" is used herein to designate a naturally occurring polymer built up of carbohydrate monomers while the term "polymerized carbohydrate" is used to designate a synthetic polymer obtained by polymerizing carbohydrate molecules, e.g. with the aid of at least bifunctional coupling or cross-linking agents. Similarly, the term "polymerized sugar alcohol" is used to designate a synthetic polymer obtained by polymerizing sugar alcohol molecules, e.g. with the aid of at least bifunctional coupling or cross-linking agents. The term paramagnetic metal species as used herein includes within its scope both paramagnetic atoms and ions.

As indicated above, the macromolecular product is preferably a material which is insoluble but swellable in water. It is well known that for example water-soluble polymeric or polymerized carbohydrates or polymerized sugar alcohols or derivatives thereof can be cross-linked with the aid of cross-linking agents which are least bifunctional to a practically endless three-dimensional network which is held together by bonds of covalent character and which is insoluble but swellable in water and aqueous media. Such insoluble products, for example those obtained cross-linking polysaccharides (e.g. dextran, starch, agarose and other polymeric carbohydrates and derivatives thereof), are well known in the form of gel particles (preferably in bead form) for use e.g. in gel chromatogrphy and also as ion-exchangers when the macromolecular gel particles are provided with ion-exchanging groups such as carboxyl groups or amino groups. The hydroxyl group containing polymers described above are preferably reacted with the cross-linking agent to produce cross-linking bridges bound to the polymers via for example ether bonds or ester bonds (e.g. carboxylic acid ester bonds, carbamic acid ester bonds, thiocarbamic acid ester bonds, etc.). Examples of ether-bound crosslinking bridges and ester-bound cross-linking bridges and methods for the production of such gel particles are for example described in GB-A-1 518 121, U.S. Pat. No. 4,225 580, GB-A-1 251 433, U.S. Pat. Nos. 3,042,667 and 3,002 823.

In accordance with one suitable and practical embodiment of the invention the molecules of the polysaccharide or of the derivative thereof etc. are cross-linked by bridges bound to these molecules by ether bonds, wherein between the ether bonds the bridges may advantageously be straight or branched aliphatic saturated hydrocarbon chains which are substituted by one or more hydroxyl groups (e.g. one to six hydroxyl groups), which contain 3-30 carbon atoms, preferably 3-20 carbon atoms, and especially 3-10 carbon atoms, and which optionally are interrupted by one or more oxygen atoms (e.g. one to six oxygen atoms). Examples of such ether-bound cross-linking bridges include —CH$_2$—CH(OH)—CH$_2$— and
—CH$_2$—CH(OH)—CH(OH)—CH$_2$— and
—CH$_2$—CH(OH)—CH$_2$—O—CH$_2$—CH(OH)—CH$_2$— and
—CH$_2$—CH(OH)—CH$_2$—O—(—CH$_2$)$_n$—O—CH$_2$—CH(OH)—CH$_2$—, where n is an integer, for example an integer from 2 to 4.

In accordance with another embodiment of the invention the molecules of the polysaccharide or of the derivative thereof are cross-linked by bridges bound to said molecules by ester bonds (which preferably are carboxylic acid ester bonds, but which for example may also be carbamic acid ester bonds or thiocarbamic acid ester bonds), the bridges between the ester bonds advantageously being straight or branched aliphatic saturated hydrocarbon chains containing 2-20 carbon atoms, preferably 2-10 carbon atoms such as 2-6 carbon atoms, optionally being interrupted by one or more oxygen atoms (e.g. one to six oxygen atoms), and optionally being substituted with one or more hydroxyl groups (e.g. one to six hydroxyl groups).

Examples of such ester-bound (in its widest significance) cross linking bridges include —O—CO—(CH$_2$)$_{n1}$—CO—O— (where n$_1$ is an integer, for example an integer from 1 to 20, preferably 2-10, especially preferably 2 to 6), —O—CO—CH$_2$—O—CH$_2$—CO—O—, —O—CO—NH—(CH$_2$)$_{n2}$—NH—CO—O— and —O—CS—NH—(CH$_2$)$_{n2}$—NH—CS—O (where n$_2$ is an integer, for example an integer from 2 to 6).

Examples of non-cross-linked macromolecular products useful according to the invention include cellulose, agarose and other insoluble polysaccharides and insoluble derivatives thereof. These can be used e.g. in the preparation of diagnostic agents for administration to body cavities having external escape ducts, e.g. the bladder, the uterus and the gastrointestinal tract.

The cross-linked macromolecular product can be obtained in the form of particles either by preparing the polymerisates in the form of larger pieces (bulk polymerization) and then disintegrating said pieces, for instance by grinding, or by directly preparing the product in the form of smaller, preferably spheroidal, particles (beads) by dispersion polymerization. Particles of the desired size range can be isolated by fractionation of the product, e.g. by sieving.

The particle size chosen will vary depending on the particular use intended for the diagnostic agent. In general, however, the particles in their water-swollen state will have a size within the range 0.01-1000 μm, preferably within the range 0.1-100 μm. In this connection, particles having a particle size within the range 0.01-5 μm, such as eg within the range of 0.1-3 μm, are considered small, whereas particles having particle size exceeding 5 μm, for instance having a particle size within the range 5-100 μm, are considered large. For parenteral use small particles, preferably particles having a particle size less than 3μm, should be used where it is intended that the particles should be able to pass blood capillaries without causing obstruction. For diagnostic agents intended for administration to body cavities having external escape ducts (e.g. the gastrointestinal tract), particles having a size within a wide range can be used. However, in order to avoid sedimentation of the particles, it is preferred that particles of a size less than 10 μm be used.

As is well known in the field of cross-linked polysaccharides, the swellability of the product in water and aqueous media can be varied by varying the cross-linking agent and/or the degree of crosslinking. In accordance with the present invention the swellability is preferably chosen such that the particles of the macromolecular product in water-swollen state contain 10-98, preferably 15-95, and especially preferably 20 to 90, percent by weight of water.

Examples of basic materials which may be cross-linked to water-insoluble but water-swellable gel particles include water soluble polysaccharides such as glucans, e.g. starch, amylose, amylopectin (including macromolecular dextrins thereof), glycogen, dextran and pullulan, fructans, e.g. inulin and levan, and other physiologically tolerable polysaccharides of vegetable, microbial or animal origin. Another example is the so called polyglucose obtained by polymerization of glucose. Ohter examples include macromolecular products obtained by cross-linking carbohydrates or sugar alcohols (e.g. mannitol and sorbitol) with at least one bifunctional cross-linking agent, e.g. with epichlorohydrin or diepoxides or corresponding halogen hydrins. An example of such a product is Ficoll (available from Pharmacia Fine Chemicals AB, Uppsala, Sweden—Ficoll is a registered Trade Mark) which is obtained by cross-linking sucrose with the aid of epichlorohydrin (vide e.g. SE-B-209 018 and U.S. Pat. No. 3,300,474). Other examples include physiologically tolerable derivatives of the basic materials exemplified above, for example hydroxyalkyl, carboxyalkyl, acyl or alkyl derivatives, e.g. hydroxyethyl, dihydroxypropyl, carboxymethyl, acetyl or methyl derivatives of the polysaccharides mentioned above. After cross-linking of such products to a three-dimensional, water-insoluble but water-swellable network the gel particles are suitable for being provided with paramagnetic metal containing substances.

The macromolecular product in the particles in the diagnostic agent of the invention is chosen according to the agent's intended use. Thus, for example, insoluble particles which are not degradable in the body may be chosen for investigation of body cavities having outward escape ducts (e.g. the gastro-intestinal tract, the bladder and the uterus). Insoluble particles which are degradable in the body to smaller, water-soluble excretable fragments may be chosen, for example, for parenteral administration. For example, the macromolecular product in the particles may be enzymatically degradable by hydrolases, e.g. endohydrolases, which hydrolyze glycosidic linkages in the macromolecular product. Thus, according to a particularly suitable embodiment of the invention macromolecular products which are degradable by α-amylase are chosen. In this case cross-linked, insoluble macromolecular products based on starch or other polysaccharides degradable by α-amylase and degradable derivatives thereof can be used. The total degree of substitution of such starch derivatives should however not be chosen to be so high as to stop the derivative being degradable, generally the average degree of substitution will often be less than 0.6 and preferably will be less than 0.5 (i.e. less than one substituent per 2 glucose units), for example less than 0.3 or 0.2 or 0.1. When particles consisting of such macromolecular products are degraded in the body, smaller, water-soluble fragments (some of which may contain the paramagnetic metal species) are formed and these fragments can be excreted with the urine. Particles based on cross-linked starch which are degradable by α-amylase are described e.g. in GB-A-1 518 121. The particles can be produced with the desired size and, if desired, can be provided with metal binding structures to which the paramagnetic metal species may be chemically bound. For example, degradable particles according to the invention having such a size (e.g. about 0.1–3 μm, for instance 0.5–2 μm in water swollen state) that they are taken up by the reticuloendothelial system (RES) of e.g. the liver after parenteral administration are of special interest, e.g. for investigations of the liver.

The macromolecular product particles in the diagnostic agent of the invention may be neutral or may have a negative or positive net charge in aqueous suspensions. For parenteral use, particles with no net charge or a negative net charge in aqueous suspensions are preferred. A negative net charge may be obtained for instance by introducing carboxyl groups or other negatively charged groups into the macromolecular product if such groups are not already present in the macromolecular product.

The non-radioactive paramagnetic metal is preferably selected from the group of elements having atomic numbers 21–29, 42, 44 and 57–70, elements having atomic numbers 24–29 or 62–69 being especially preferred. Examples of suitable lanthanides include gadolinium, europium, dysprosium, holmium and erbium. Examples of other suitable elements include manganese, iron, nickel, chromium and copper.

The paramagnetic metal species may in one embodiment of the invention be chemically bound in the macromolecular product. The polymeric or polymerized carbohydrate or the polymerized sugar alcohol or derivative thereof used in the preparation of the diagnostic agent of the invention contains or may be provided with binding structures to which the paramagnetic metal species may be bound. It is well known that many structures bind metals of the types which are of interest in this connection. Such structures are easily introduced into polymeric or polymerized carbohydrates or polymerized sugar alcohols or derivatives thereof if not already present in these macromolecules. For example, several such insoluble products have been used for extracting heavy metal ions from aqueous solutions and for binding metallic radionuclides. As it is desirable that the metal species is firmly bound to the macromolecular product, structures to which the metal species is bound in a complex can be used; structures wherein the metal species is bound in a chelate complex being preferred. Many groups are known which bind metal ions in chelate complexes in which complexes the metal can be included e.g. in a 4-, 5- or 6-membered ring comprising said metal and two metal-coordinating atoms.

Preferably the chelate complex comprises at least two 5- or 6-membered rings comprising the metal, especially four to eight 5- or 6-membered rings. Such 5- and 6-membered rings comprise the metal and two metal-coordinating atoms, separated from each other by two or three atoms respectively According to another aspect, one of the metal-coordinating atoms is preferably a nitrogen atom and the other a nitrogen atom, a sulphur atom or an oxygen atom. The nitrogen atom can, for instance, be the nitrogen atom in an amino, imino or nitrilo group. The sulphur atom can, for instance, be the sulphur atom in a mercapto, thioether or thiono group. The oxygen atom can, for instance, be an oxygen atom in a keto, carboxylate, sulphonate, sulphate, phosphonate, phosphate, nitrate, hydroxyl or ether group. The metal-coordinating atoms are members of chelate-forming groups which preferably contain at least two sequences, which may be equal or different, and which, in addition to the metal-coordinating atoms, preferably contain 2 or 3 carbon atoms (in the case of 5- and 6-membered rings respectively) in the chelate complex, one of the carbon atoms optionally being replaced by an oxygen, sulphur or nitrogen atom. For instance the chelate-forming groups may have the general formula

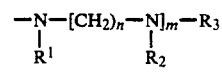

wherein n is 2 or 3, m is an integer 1, 2, 3 or higher, generally lower than 1000, e.g. lower than 100 or lower than 50 such as 1–50, or 2–6, and $R_1$, $R_2$ and $R_3$, which may be equal or different, each represents a hydrogen atom or a group —$CH_2$—COOH or —$CH_2$—$CH_2$—COOH. The carboxymethyl and the carboxyethyl groups may be replaced by sulphomethyl phosphomethyl or aminoethyl groups or by sulphoethyl, phosphoethyl or aminopropyl groups respectively, or by other equivalent groups. Furthermore the chelate-forming groups may of course be used in salt form.

The chelate-forming groups may be covalently bound to hydroxyl groups of the polymeric or polymerized carbohydrate or polymerized sugar alcohol or derivative thereof, e.g. by methods known per se. For instance, when using an aminopolycarboxylic acid, such as ethylenediaminetetraacetic acid (EDTA), diethylenetriaminepentaacetic acid (DTPA), triethylenetetraaminehexaacetic acid (TTHA) or N-hydroxyethylethylenediaminetriacetic acid (HEDTA), to establish chelate-forming groups, a carboxylic group of said acids may be utilized to produce an ester bond to the basic molecule of the macromolecular product by reaction, e.g. in the presence of a carbodiimide or another coupling agent. Anhydrides or acid halides of such polycarboxylic acids can also be used. Alternatively, an amino-polycarboxylic acid containing a primary or secondary amino group can be reacted with a macromolecular substance containing carboxylic groups in order to form an amide bond, e.g. by using conventional methods for establishing such bonds.

Reactive groups may also be introduced into the basic molecule of the macromolecular product, e.g. a polysaccharide, for example in ways known per se; such reactive groups can then be reacted with thiol or amino groups or other nucleophilic moieties in the substance used for the introduction of chelate-forming groups. Examples of such groups are aldehyde and keto groups, halogenoacetyl, azide, isocyanate, isothiocyanate, s-triazinyl and divinylsulphone groups, carbonic acid ester groups, imidocarbonic acid ester groups (formed by cyanogen bromide activation), oxirane groups and groups which are easily converted to oxirane derivatives and reactive disulphides. On the other hand, activation of hydroxyl groups of the basic molecule of the macromolecular product with a base will enable a reaction with electrophilic moieties in the substance used for the introduction of chelate-forming groups to occur.

The complete chelate-forming group may be bound directly to the basic molecule of the macromolecular product or may be built up successively by binding a starting material for said group to said basic molecule and then modifying said starting material chemically. For instance, a compound of the general formula $H_2N-[(CH_2)_n-NH]_m-H$, wherein m and n are as defined above, may first be bound to said basic molecule, e.g. by methods known per se, whereafter the amino groups can be carboxymethylated or carboxyethylated to the desired extent.

If desired, a bridging group can be introduced between the chelate-forming groups and the basic molecule of the macromolecular product, e.g. in a manner known per se.

The paramagnetic metal can for example be bound to the macromolecular product by reacting the intermediate macromolecular substance containing chelate-forming groups with an excess of a watersoluble salt of the paramagnetic metal in aqueous solution at an appropriate pH-value, usually 2-7, e.g. 5-6.

In an alternative embodiment of the invention the paramagnetic metal species may be present in cavities within the macromolecular product, in the form of an insoluble or sparingly soluble substance or composition. The incorporation of the paramagnetic metal species within the macromolecular carrier product can be achieved in several ways.

In one method dry or incompletely water-swollen particles of a swellable macromolecular product may be swelled in a solution, preferably an aqueous solution, of a salt of the paramagnetic metal, for instance the chloride of said metal, whereafter the particles are dried. The particles are then swelled again in a solution, preferably an aqueous solution, of a substance which is capable of precipitating the metal in the form of an insoluble or sparingly soluble material, compound or complex. For instance the precipitating substance may be a soluble phosphate, such as sodium phosphate, when the phosphate of the paramagnetic metal is insoluble or sparingly soluble in the medium in which the particles are swelled. Alternatively, the precipitating substance may be an alkali metal hydroxide when the hydroxide of the paramagnetic metal is insoluble or sparingly soluble in the medium in which the particles are swelled.

According to another method, dry or incompletely water swollen particles of a swellable macromolecular product are swelled in a solution comprising a solvent in which the particles swell, e.g. water or dimethylsulfoxide, and one or more reagents of which at least one comprises the paramagnetic metal species in a suitable chemical form, and which reagents (optionally in contact with the macromolecular product) produce by a chemical reaction (which may involve the macromolecular product), for example a redox process, the metal species in elemental state or in the state of an insoluble or sparingly soluble chemical compound containing the metal, said metal or compound being finely dispersed in the cavities of the macromolecular product.

According to another method the preparation of the macromolecular product is prepared by a process involving a cross-linking reaction carried out in a medium in which microparticles of the paramagnetic metal or a compound or complex thereof are dispersed, said compound or complex being insoluble or sparingly soluble in said medium. Thus the paramagnetic metal species will become entrapped in a very finely dispersed form in cavities formed in the three-dimensional network of the particles of the macromolecular product.

Where the paramagnetic metal species is incorporated as a complex, this is preferably a chelate complex which is insoluble or sparingly soluble in aqueous media.

Preferably such a chelate complex comprises at least two 5- or 6-membered rings comprising the metal, especially four to eight 5- or 6-membered rings. Such 5- and 6-membered rings comprise the metal and two metal-coordinating atoms, separated from each other by two or three atoms respectively. One of the metal-coordinating atoms is preferably a nitrogen atom and the other a nitrogen atom, a sulphur atom or an oxygen atom. The nitrogen atom can, for instance, be the nitrogen atom in an amino, imino or nitrilo group. The sulphur atom can, for instance, be the sulphur atom in a mercapto, thioether or thiono group. The oxygen atom can, for instance, be an oxygen atom in a carboxylate, sulphonate, sulphate, keto, phosphonate, phosphate, nitrate, hydroxyl or ether group. The metal-coordinating atoms are members of chelate-forming groups which preferably contain at least two sequences, which may be equal or different, which in addition to the metal-coordinating atoms preferably contain 2 or 3 carbon atoms (in the case of 5- and 6-membered rings respectively) in the chelate complex, one of the carbon atoms optionally being replaced by an oxygen, sulphur or nitrogen atom.

As mentioned above, the macromolecular product particles may in aqueous suspensions have a net charge in which case the diagnostic agent should include a physiologically acceptable counterion. Examples of useful cations in this connection include sodium and potassium ions and the cations of non-toxic amines such as e.g. tris(hydroxymethyl)aminomethane, ethanolamine, diethanolamine and N-methylglucamine. Examples of useful anions include chloride ions and the anions of non-toxic organic acids.

The diagnostic agent according to the invention may e.g. be in the form of a suspension of the macro-molecular product particles in an aqueous medium or may be in dry form, e.g. in the form of a powder or tablets to be used for the preparation of a suspension just before administration. The agent may also be in the form of capsules or coated tablets to be administered orally, in which case the coating of the tablet or capsule is dissolved in the gastro-intestinal tract to release the macromolecular product particles. Uncoated tablets, which are disintegrated in the gastrointestinal tract may also be used for oral administration.

For parenteral administration a suspension in a sterile physiologically acceptable medium is preferably used, e.g. an isotonic aqueous solution. For administration to body cavities having external escape ducts (e.g. the gastrointestinal tract (for example by oral or rectal administration), the bladder and the uterus), a suspension in a physiologically acceptable medium, e.g. an aqueous suspension, optionally containing viscosity-increasing substances may conveniently be used. The aqueous suspension may be adjusted to the desired pH-value by means of a physiologically acceptable buffer.

Also other additives such as those which are conveniently used within the pharmaceutical industry can be added to the various different formulations; for instance, flavourants and dyestuffs can be incorporated into compositions for oral use. Thus it may be stated that the diagnostic agents according to the present invention may conveniently be formulated to contain at least one pharmaceutical carrier or excipient, and may optionally contain viscosity enhancing agents, osmolality regulators, colouring agents, flavouring agents or dispersants.

The concentration of the paramagnetic metal in the diagnostic agent will be dependent on the administration form and on the particular organs or tissues to be studied. Generally the total dosage will be in the range of $10^{-6}$ to 10, preferably about $10^{-3}$ to $10^{-1}$, mmol of the paramagnetic metal species per kg bodyweight. The paramagnetic metal content of the macromolecular product will generally be 0.001–30 percent by weight, preferably more than 0.01 percent by weight, e.g. more than 0.1 per cent by weight, and, for example, lower than 20 percent by weight or lower than 10 percent by weight, calculated on the total weight of the macromolecular product in dry substance form.

The concentration of the macromolecular product in a suspension to be used in NMR or ultrasound diagnosis will generally be higher than 0.01 per cent by weight, for instance higher than 0.1 per cent by weight, for example higher than 1 per cent by weight, and lower than 35 percent by weight, for example lower than 25 percent by weight, e.g. lower than 15 percent by weight, calculated on the total weight of the suspension. For example, the concentration may conveniently be within the range 0.1-10 percent by weight, calculated on the total weight of the suspension. (The weight of the macromolecular product is that of the dry substance.)

The diagnostic agent according to the invention can be used in NMR imaging because the paramagnetic metal species carried by the macromolecular product reduces the relaxation times. It can also be used in NMR examinations due to its effect on the chemical shifts or it can be used in ultrasound examinations due to its effect on sound velocity.

According to a further aspect of the invention we provide a method of diagnosis which method comprises administering to a human or non-human animal body or to a selected region thereof a contrast effective amount of the diagnostic agent of the invention and generating an NMR or ultrasound image of said body or said region. We further provide a method of producing an image capable of use in diagnosis, which method comprises administering to a human or non-human animal body or to a selected region thereof a contrast effective amount of the diagnostic agent of the invention and generating an NMR or ultrasound image of said body or said region, and optionally fixing said image in hardcopy form, e.g. in printed graphic or in photographic negative or positive form.

According to a still further aspect of the invention we provide a process for the preparation of a water-insoluble, paramagnetic metal species-containing macromolecular material comprising chemically binding a non-radioactive paramagnetic metal species to or trapping or depositing a non-radioactive paramagnetic metal species in a water-insoluble or sparingly soluble form within a physiologically tolerable, water-insoluble, particulate macromolecular product comprising at least one material selected from the group comprising polymeric and polymerized carbohydrates and polymerized sugar alcohols and derivatives thereof.

According to a further aspect of the invention we provide a process for preparing a diagnostic agent containing a non-radioactive paramagnetic metal species, characterized in that said process comprises admixing with a least one pharmaceutical carrier or excipient a physiologically tolerable, water-insoluble, hydroxyl group-containing macromolecular product in particulate form, said macromolecular product comprising at least one material selected from the group comprising polymeric and polymerized carbohydrates and polymerized sugar alcohols and derivatives thereof.

According to another feature of the invention we provide the use for the manufacture a diagnostic agent for use in a method of diagnosis practised on the human or animal body of a non-radioactive paramagnetic metal species and a physiologically tolerable, water-insoluble, hydroxyl-group containing, particulate macromolecular product comprising at least one material selected from the group comprising polymeric and polymerized carbohydrates and polymerized sugar alcohols and derivatives thereof.

The invention will no be further illustrated by means of the following non-limiting Examples. Percentages and ratios are by weight unless stated otherwise.

The following abbreviations are used in the Examples:
DMF = dimethyl formamide
DMSO = dimethyl sulphoxide
DOTA = 1,4,7,10-tetraazacyclododecane N,N',N'',N''' tetraacetic acid
DTPA = diethylenetriaminepentaacetic acid
EDTA = ethylenediaminetetraacetic acid
TTHA = triethylenetetraaminehexaacetic acid
SRRE = specific relaxation rate ($T_1$) enhancement
$W_r$ = water regain (definition given in Example 1)
D = water-swelled diameter
$D_{av}$ = average water-swelled diameter $T_{\frac{1}{2}}$=half life by α-amylase degradation (vide Example 1)

$T_1$=spin lattice relaxation time

EXAMPLE 1

Starch particles in the form of gel beads with various average diameters, half-lifes ($T_{\frac{1}{2}}$) in 240 IU/l of α-amylase at pH 7.0 and 37° C. and water regain ($W_r$) were prepared by cross-linking hydrolyzed potato starch with epichlorohydrin using the method described in GB-A-1251433 and U.S. Pat. No. 4,126,669. The products were analyzed as described in those patents. In the following Examples particles with the following characteristics were used:

| Particles | Water swelled average diameter μm | | Half life $T_{\frac{1}{2}}$ min | Water regain $W_r$ |
|---|---|---|---|---|
| A | 50 | (SD 10) | 31 | |
| | | | | 4.7 |
| B | 1.5 | (SD 0.4) | 20 | 12.5 |
| C | 102 | (SD 30) | 55 | |
| | | | | 4.7 |
| D | 1.6 | (SD 0.4) | 125 | 8.6 |
| E | 9 ± 5 | | 9 | 4.2 |

$W_r$ is defined as the weight of water (g) taken up by 1 g of dry particles. The percentage of water within the swelled particle is $$100 \cdot \frac{W_r}{W_r + 1}.$$

EXAMPLE 2

1.5 g of the bisanhydride of diethylenetriaminepentaacetic acid, (prepared from DTPA according to the method described in J. Pharm. Sci. 64, (1975) 704 by W. C. Eckelman et al.) were added to a suspension of 2.0 g starch gel beads (Example 1, type A) in 60 ml dry dimethyl sulphoxide (DMSO) at ambient temperature. The suspension was agitated at ambient temperature for 24 hours. 100 ml of distilled water were added while the suspension was cooled with an ice-water bath. The suspension was agitated at ambient temperature for 1 hour and the particles were isolated by centrifugation. The particles were washed 6 times by alternate resuspending in distilled water and centrifugation. The particles were suspended in 50 ml distilled water, the pH-value was adjusted to 6.2 and a solution of 0.92 g $FeCl_2.4H_2O$ in 10 ml distilled water was added during agitation. The pH-value was adjusted to 5.1 and the suspension was agitated for 2 hours.

The particles were isolated by centriguation, washed with distilled water, dialyzed with 0.9 per cent (w/v) NaCl until the solutions were free from paramagnetic compounds (about 5 days), washed with distilled water and dried in vacuo at 50° C.

0.9 g of dark yellow particles containing 5.6 percent (w/w) Fe was obtained. $W_r$ 21.1. Half life in amylase solution 240 IU/l ($T_{\frac{1}{2}}$) 60 min.

Specific relaxation rate enhancement (SRRE) was measured in an NMR proton spin analyzer (RADX CORP. Houston, Tex., U.S.A.) at 10 MHz in glycerol:-water (1.2.13) (v:v) at 37° C. SRRE 0.22 $s^{-1}$ $mM^1$. Diameter (D) 30–100 μm (water-swelled particles, 90 per cent within the given range).

EXAMPLE 3

DTPA was bound to 2.0 g starch gel beads (Example 1, type A) as described in Example 2. The particles were suspended in 50 ml distilled water. The pH-value was adjusted to 6.1 and a solution of 1.15 g $CuSO_4.5H_2O$ in 10 ml distilled water was added during agitation, the pH-value was adjusted to 5.2 and the suspension was agitated for 1 hour. The particles were purified and isolated as described in Example 2. 1.2 g of blue green particles containing 8.1 percent (w/w) Cu were obtained. $W_r$ 7.9. $T_{\frac{1}{2}}$ >24 h. SRRE 0.12 $s^{-1}$ $mM^{-1}$. D 25–70 μm (90 percent within the given range).

EXAMPLE 4

DTPA was bound to 0.30 g starch gel beads (Example 1, type A) as described in Example 2 by using 0.50 g of the bisanhydride of DTPA. The particles were suspended in 30 ml of distilled water, the pH-value was adjusted to 5.8 and a solution of 0.20 g $GdCl_3.6H_2O$ in 20 ml distilled water was added during agitation. The pH-value was adjusted to 5.8 and the suspension was agitated for 1 hour. The particles were purified and isolated as described in Example 2. 0.25 g of white particles containing 1.5 percent (w/w) Gd was obtained. The particles swell in water. $T_{\frac{1}{2}}$ 1 h. On suspending 30 mg of the particles in 5 ml glycerol:water (1:2.13) (v:v), the spin lattice relaxation time ($T_1$) was reduced from 1926 ms to 443 ms (37° C., 10 MHz). $D_{av}$ 50 μm.

EXAMPLE 5

DTPA was bound to 2.0 g starch gel beads (Example 1, type A) as described in Example 2. The particles were suspended in 50 ml distilled water, the pH-value was adjusted to 6.2 and a solution of 1.77 g $ErCl_3$ (containing 40 percent of water) in 10 ml distilled water was added during agitation, the pH-value was adjusted to 5.1 and the suspension was agitated for 30 minutes. The particles were purified and isolated as described in Example 2. 1.77 g of white particles containing 8.5 percent (w/w) Er were obtained. $W_r$ 9.6. $T_{\frac{1}{2}}$ 6 h. SRRE 0.11 $s^{-1}mM^{-1}$. D 30–100 μm (90 percent within the given range).

EXAMPLE 6

1.0 g starch gel beads (Example 1, type A) was swelled in 15 ml distilled water, 1.0 ml epichlorohydrin and 3.5 ml 2M NaOH were gradually added during 2 hours while the suspension was shaken at ambient temperature. 6 mg sodium borohydride were added and the suspension was shaken for 24 hours at ambient temperature. The particles were collected on a filter, washed on the filter with distilled water and resuspended in 25 ml distilled water. 2.4 g of 1,6-diaminohexane were added and the suspension was shaken for 22 hours at ambient temperature. The particles were collected on a filter and washed on the filter with distilled water.

The particles were resuspended in 30 ml distilled water. 4.8 g of the bisanhydride of DTPA were added and the suspension was shaken for 17 hours at ambient temperature. The pH-value was adjusted to 10, the particles were collected on a filter, washed thoroughly with distilled water and resuspended in 50 ml of distilled water. The pH-value was adjusted to 6.0, a solution of 0.5 g $GdCl_3.6H_2O$ in 20 ml distilled water was added and the pH-value was adjusted to 5.1. The suspension was shaken for 30 minutes, the particles were collected on a filter, washed thoroughly with distilled water and dried in vacuo at 50° C. 0.8 g of white particles containing 3.2 percent (w/w) Gd was obtained. The particles swell in water. $T_{\frac{1}{2}} > 25$ h. On suspending 30 mg of the particles in 5 ml glycerol:water (1:2.13) (v:v), $T_1$ was reduced from 1926 ms to 450 ms. $D_{av}$ 50 μm.

EXAMPLE 7

A solution of 1.83 g 1,1'-carbonyldiimidazole in 15 ml dry acetone was added to a suspension of 1.5 g starch gel beads (Example 1, type A) in 20 ml of dry acetone. The suspension was shaken for 20 minutes at ambient temperature and the solvent was removed after centrifugation. The particles were washed with acetone, resuspended in 50 ml acetone and 3.9 g 1,6-diaminohexane were added. The suspension was shaken for 18 hours at ambient temperature, the solvent was removed after centrifugation and the particles were washed with acetone.

The particles were resuspended in dry dimethylformamide (DMF), 4.0 g of the bisanhydride of DTPA were added and the mixture shaken for 24 hours at ambient temperature. 100 ml of distilled water were added, the pH-value was adjusted to 10 and the suspension was agitated for 30 minutes at ambient temperature. The suspension was centrifuged, the supernatant was removed and the particles were thoroughly washed with distilled water. The particles were resuspended in 30 ml of distilled water, the pH-value was adjusted to 6.0 and a solution of 1.0 g $GdCl_3.6H_2O$ in 20 ml distilled water was added. The pH-value was adjusted to 5.8 and the suspension was agitated for 30 minutes at ambient temperature followed by centrifugation. The supernatant was removed and the particles were thoroughly washed with distilled water. The particles were dried in vacuo at 50° C. 1.2 g of white particles containing 17.9 percent (w/w) Gd were obtained. The particles swell in water. $T_{\frac{1}{2}} > 24$ hours. On suspending 30 mg of the particles in 5 ml glycerol:water (1:2.13) (v:v), $T_1$ was reduced from 1926 ms to 380 ms. $D_{av}$ 45 μm.

EXAMPLE 8

2.5 g of starch gel beads (Example 1, type A) were suspended in 25 ml of dry acetone. 2.0 ml of triethylamine were added and the suspension was cooled to 0° C. A solution of 2.5 g p-toluenesulphonyl chloride in 6 ml dry acetone, cooled to 0° C., was added to the agitated suspension. The suspension was agitated for 1 hour at 0° C. and for 23 hours at 5° C. The suspension was centrifuged, the supernatant removed and the particles washed with cold acetone.

The particles were resuspended in 30 ml of dry methanol. 100 ml of a 5.3M solution of ammonia in methanol were added and the suspension was agitated for 20 hours at ambient temperature. The suspension was centrifuged, the supernatant was removed and the particles were washed with methanol. The particles were resuspended in 100 ml of dry DMF. 4.9 g of the bisanhydride of DTPA were added, the suspension was treated as in Example 7 and the resulting DTPA particles were resuspended in 100 ml distilled water, the pH-value was adjusted to 6.1 and a solution of 1.5 g $GdCl_3.6H_2O$ in 20 ml distilled water was added. The pH-value was adjusted to 5.0 and the suspension was agitated for 30 minutes at ambient temperature followed by centrifugation. The supernatant was removed and the particles were thoroughly washed with distilled water. The particles were dried in vacuo at 50° C. 2.1 g of white particles containing 19.1 percent (w/w) Gd were obtained. The particles swell in water. $T_{\frac{1}{2}} > 24$ hours. On suspending 30 mg of the particles in 5 ml glycerol:water (1:2.13) (v:v), $T_1$ was reduced from 1926 ms to 455 ms. $D_{av}$ 45 μm.

EXAMPLE 9

2.5 g of starch gel beads (Example 1, type B) were suspended in 25 ml of dry acetone. 2.0 ml of triethylamine were added and the suspension was cooled to 0° C. A solution of 2.5 g p-toluenesulphonyl chloride in 6 ml dry acetone, cooled to 0° C., was added to the agitated suspension. The suspension was agitated for 1 hour at 0° C. and for 23 hours at 5° C. The suspension was centrifuged, the supernatant removed and the particles washed with cold acetone.

The particles were resuspended in 80 ml dry acetone, 5.3 g of 1,6-diaminohexane were added and the suspension was agitated for 20 hours at ambient temperature. The suspension was centrifuged, the supernatant was removed and the particles were washed with dry acetone and treated with DTPA as in Example 8. The pH-value of the DTPA-particle suspension was adjusted to 5.7 and a solution of 0.87 g $GdCl_3.6H_2O$ in 20 ml of distilled water was added. The pH-value was adjusted to 5.1 and the suspension was treated and the particles isolated as in Example 8. 2.0 g of white particles containing 10.7 percent (w/w) Gd were obtained. The particles swell in water. $T_{\frac{1}{2}} > 24$ hours. On suspending 30 mg of the particles in 5 ml glycerol:water (1:2.13) (v:v), $T_1$ was reduced from 1926 ms to 479 ms. $D_{av}$ 1.5 μm.

EXAMPLE 10

DTPA was bound to 2.0 g starch gel beads (Example 1, type B) as described in Example 2. The particles were suspended in 50 ml distilled water, the pH-value was adjusted to 6.1 and a solution of 1.23 g $CrCl_3.6H_2O$ in 10 ml distilled water was added. The pH-value was adjusted to 5.0 and the suspension was agitated for 35 minutes. The particles were purified and isolated as described in Example 2. 1.23 g of violet particles containing 4.0 percent (w/w) Cr were obtained. $W_r$ 4.7. $T_{\frac{1}{2}} > 24$ hours. SRRE 0.91 $s^{-1}mM^{-1}$. $D_{av}$ 1.2 μm.

EXAMPLE 11

DTPA was bound to 2.0 g starch gel beads (Example 1, type B) as described in Example 2. The particles were suspended in 50 ml distilled water, the pH-value was adjusted to 6.2 and a solution of 0.91 g $MnCl_2.4H_2O$ in 10 ml distilled water was added, the pH-value was adjusted to 5.2 and the suspension was agitated for 40 minutes. The particles were purified and isolated as described in Example 2. 0.91 g of white particles containing 5.9 percent (w/w) Mn was obtained. $W_r$ 10. $T_{\frac{1}{2}} > 24$ h. SRRE 2.95 $s^{-1}mM^{-1}$. $D_{av}$ 1.4 μm.

EXAMPLE 12

DTPA was bound to 2.0 g starch gel beads (Example 1, type B) as described in Example 2. The particles were suspended in 50 ml distilled water, the pH-value was adjusted to 6.3 and a solution of 1.25 g $FeCl_3.6H_2O$ in 10 ml distilled water was added. The pH-value was adjusted to 5.1 and the suspension was agitated for 1 hour. The particles were purified and isolated as described in Example 2. 1.25 g of dark yellow particles containing 7.8 percent (w/w) Fe were obtained. $W_r$ 23.2. $T_{\frac{1}{2}} > 24$ h. SRRE 0.52 $s^{-1}mM^{-1}$. $D_{av}$ 1.9 μm.

EXAMPLE 13

DTPA was bound to 2.0 g starch gel beads (Example 1, type B) as described in Example 2. The particles were suspended in 50 ml distilled water, the pH-value was adjusted to 6.1 and a solution of 1.72 g $GdCl_3.6H_2O$ in 10 ml distilled water was added during agitation, the pH-value was adjusted to 5.2 and the suspension was agitated for 50 minutes. The particles were purified and isolated as described in Example 2. 1.72 g of white particles containing 12.2 per cent (w/w) Gd were obtained. $W_r$ 7.4. $T_{\frac{1}{2}} > 24$ h. SRRE 6.4 $s^{-1}mM^{-1}$. $D_{av}$ 1.3 μm.

EXAMPLE 14

2.6 g triethylenetetraaminehexaacetic acid (TTHA) and 100 mg of 4-dimethylaminopyridine were added to a suspension of 2.0 g of starch gel beads (Example 1, type B) in 175 ml dry DMSO. 5.0 g N-(3-dimethylaminopropyl)-N'-ethylcarbodiimide were added and the suspension was agitated for 22 hours at ambient temperature. The agitated reaction mixture was cooled in an ice bath, 100 ml of distilled water were gradually added, the ice bath was removed, the mixture was stirred for 30 minutes and the pH-value was adjusted to 6.5. A solution of 2.15 g $GdCl_3.6H_2O$ in 20 ml distilled water was added, the pH-value was adjusted to 5.7 and the suspension was agitated for 30 minutes. The particles were purified and isolated as described in Example 2. 1.4 g of white particles containing 4.2 per cent (w/w) Gd were obtained. $W_r$ 4.3. $T_{\frac{1}{2}} > 24$ h. SRRE 3.4 $s^{-1}mM^{-1}$. $D_{av}$ 1.1 μm.

EXAMPLE 15

TTHA was bound to 2.0 g of starch gel beads (Example 1, type B) as described in Example 14.

The pH-value was adjusted to 6.5 and a solution of 1.4 g $MnCl_2.4H_2O$ in 20 ml distilled water was added. The pH-value was adjusted to 5.7 and the suspension was agitated for 30 minutes. The particles were purified and isolated as described in Example 2. 1.7 g of white particles containing 0.9 per cent (w/w) Mn were obtained. $W_r$ 4.6. $T_{\frac{1}{2}} > 24$ h. SRRE 4.6 $s^{-1}mM^{-1}$. $D_{av}$ 1.1 μm.

EXAMPLE 16

1.5 g of starch gel beads (Example 1, type B) were swelled in 30 ml of distilled water, 1.6 ml of epichlorohydrin and 5.2 ml of 2M NaOH were gradually added during 2 hours while the suspension was shaken at ambient temperature. 9 mg sodium borohydride were added and the suspension was shaken for 24 hours at ambient temperature. The suspension was centrifuged, the supernatant was removed and the particles were washed with distilled water followed by resuspension in 50 ml of distilled water. 2.4 g of 1,6-diaminohexane were added, and the suspension was shaken for 22 hours at ambient temperature. The suspension was centrifuged, the supernatant was removed, the particles were washed with distilled water followed by washing with dry DMF.

The particles were resuspended in dry DMF, 5.4 g of the bisanhydride of DTPA were added and the suspension was agitated for 17 hours at ambient temperature. The pH-value was adjusted to 10, the suspension was centrifuged, the supernatant was removed and the particles were washed with distilled water. The particles were resuspended in 50 ml of distilled water, the pH-value was adjusted to 6.0, a solution of 0.94 g $GdCl_3.6H_2O$ in 20 ml distilled water was added and the pH-value was adjusted to 5.1. The suspension was agitated for 30 minutes, the supernatant was removed and the particles were thoroughly washed with distilled water. The particles were dried in vacuo at 50° C. 1.2 g of white particles containing 16.2 percent (w/w) Gd were obtained. The particles swell in water. $T_{\frac{1}{2}} > 24$ hours. On suspending 30 mg of the particles in 5 ml glycerol:water (1:2.13) (v:v), $T_1$ was reduced from 1926 ms to 153 ms. $D_{av}$ 1.2 μm.

EXAMPLE 17

A solution of 0.6 g 1,1'-carbonyldiimidazole in 15 ml of dry acetone was added to a suspension of 1.0 g of starch gel beads (Example 1, type B) in 20 ml of dry acetone. The suspension was shaken for 20 minutes at ambient temperature, and the solvent was removed after centrifugation. The particles were washed with acetone, resuspended in 50 ml of acetone and 2.3 g of 1,6-diaminohexane were added. The suspension was shaken for 18 hours at ambient temperature, the solvent was removed after centrifugation and the particles were washed with acetone.

The particles were resuspended in dry DMF, 1.3 g of the bisanhydride of DTPA were added and the mixture was agitated for 24 hours at ambient temperature. 100 ml of distilled water was added, the pH-value was adjusted to 10 and the suspension was agitated for 30 minutes at ambient temperature. The suspension was centrifuged, the supernatant was removed and the particles were thoroughly washed with distilled water. The particles were resuspended in 30 ml of distilled water, the pH-value was adjusted to 6.1 and a solution of 1.36 g $GdCl_3.6H_2O$ in 20 ml distilled water was added. The pH-value was adjusted to 5.3 and the suspension was shaken for 30 minutes followed by centrifugation. The supernatant was removed and the particles were thoroughly washed with distilled water. The particles were dried in vacuo at 50° C. 0.7 g of white particles containing 2.7 percent (w/w) Gd was obtained. The particles swell in water. $T_{\frac{1}{2}}$ 2 h. SRRE 1.9 $s^{-1}mM^{-1}$. $D_{av}$ 1.5 μm.

EXAMPLE 18

1.5 g of starch gel beads (Example 1, type B) were swelled in 30 ml of distilled water, 1.57 ml of epichlorohydrin and 5.2 ml of 2M NaOH were gradually added during 2 hours while the suspension was shaken at ambient temperature. 9 mg of sodium borohydride were added and the suspension was shaken for 24 hours at ambient temperature. The suspension was centrifuged, the supernatant was removed and the particles were washed with distilled water and resuspended in 50 ml of distilled water. 1.6 g of diethylenetriamine and 1 ml of a 0.2M solution of $NaHCO_3$ in distilled water were added and the suspension was agitated for 22 hours at ambient temperature. The suspension was centrifuged, the supernatant was removed and the particles were washed with distilled water, 0.1M acetic acid and finally again with distilled water.

The particles were resuspended in 50 ml of distilled water, a solution of 5.7 g of chloroacetic acid in 30 ml distilled water was adjusted to the pH-value of 7.0 with 2M NaOH and 1M $NaHCO_3$ and the solution was added to the suspension. The suspension was agitated for 17 hours at ambient temperature and the suspension was centrifuged. The supernatant was removed and the particles were thoroughly washed with distilled water.

The particles were resuspended in 50 ml of distilled water and the pH-value was adjusted to 6.0. A solution of 0.94 g GdCl$_3$.6H$_2$O in 20 ml water was added, the pH-value was adjusted to 5.8 and the suspension was agitated for 30 minutes followed by centrifugation. The supernatant was removed and the particles were thoroughly washed with distilled water. The particles were dried in vacuo at 50° C. 1.1 g of white particles containing 2.1 per cent (w/w) Gd were obtained. The particles swell in water. T$_{\frac{1}{2}}$>24 hours. On suspending 30 mg of the particles in 5 ml glycerol:water (1:2.13) (v:v), T$_1$ was reduced from 1926 ms to 1147 ms. D$_{av}$ 1.5 μM.

EXAMPLE 19

A solution of 0.9 g 1,1'-carbonyldiimidazole in 30 ml dry acetone was added to a suspension of 2.0 g starch gel beads (Example 1, type B) in 60 ml of dry acetone. The suspension was agitated for 30 minutes at ambient temperature, centrifuged and the supernatant was removed. The particles were washed with acetone and resuspended in 40 ml of acetone. 2.4 g triethylenetetraamine were added and the suspension was agitated for 20 hours at ambient temperature. The mixture was centrifuged, the supernatant was removed, the particles were first washed with acetone and then with distilled water.

The particles were resuspended in 50 ml of distilled water. 3.2 g of bromoacetic acid were added. The pH-value was adjusted to 9.5, the mixture was shaken for 24 hours and 2M NaOH were added in order to keep the pH-value at 7 to 9. The suspension was centrifuged, the supernatant was removed, the particles were washed with distilled water and the particles were resuspended in 50 ml of distilled water. The pH-value was adjusted to 6.0, a solution of 0.8 g of EuCl$_3$.6H$_2$O in 20 ml of distilled water was added, the pH-value was adjusted to 5.0 and the suspension was agitated for 30 minutes. The suspension was centrifuged, the supernatant was removed and the particles were thoroughly washed with distilled water. The particles were dried in vacuo at 50° C. 1.5 g of white particles containing 1.0 percent (w/w) Eu were obtained. W$_r$ 13.3. T$_{\frac{1}{2}}$4.5 h. SRRE 0.21 s$^{-1}$mM$^{-1}$. D$_{av}$ 1.5 μm.

EXAMPLE 20

A solution of 0.9 g 1,1'-carbonyldiimidazole in 30 ml dried acetone was added to a suspension of 2.0 g starch gel beads (Example 1, type B) in 60 ml of dry acetone. The suspension was agitated for 30 minutes at ambient temperature, centrifuged and the supernatant was removed. The particles were washed with acetone and resuspended in 40 ml acetone. 3.9 g pentaethylenehexamine were added and the suspension was agitated for 20 hours at ambient temperature.

The particles were then treated as in Example 19, replacing 3.2 g of bromoacetic acid with 4.8 g. The pH-value of the resuspended particles was adjusted to 5.5, a solution of 3.2 g of FeCl$_3$.6H$_2$O in 20 ml of distilled water was added, the pH-value was adjusted to 5.3 and the suspension was agitated for 30 minutes. The suspension was centrifuged, the supernatant was removed and the particles were thoroughly washed with distilled water. The particles were dried in vacuo at 50° C. 1.7 g of white particles containing 4.6 percent (w/w) Fe were obtained. W$_r$ 12.7. T$_{\frac{1}{2}}$>24 hours. SRRE 0.11 s$^{-1}$mM$^{-1}$. D$_{av}$ 1.5 μm.

EXAMPLE 21

10 g of starch microspheres (Example 1, type C) were suspended and swelled in 150 ml of an aqueous solution of 15 g sodium hydroxide and 25 g sodium chloroacetate. The mixture was stirred at 40° C. overnight. The microspheres were collected on a filter and washed by suspending and stirring followed by filtration using acetone, ethanol and water in succession. The water suspension was neutralized to pH 5 with acetic acid. This was follwed by further washing with ethanol and drying in vacuo at 60° C. for 24 hours. 9.75 g of carboxymethyl gel beads were obtained. The product contained 2.1 meq. of carboxylate groups per g. W$_r$ 10.9 D$_{av}$ 140 μm.

EXAMPLE 22

1 g of carboxymethylated starch gel beads (Example 21) was suspended and swelled in 5 ml of water. The pH-value was adjusted to 8.4. A solution of 0.2 g MnCl$_2$.2H$_2$O in 5 ml of water was added and the mixture was stirred for 5 hours at ambient temperature. The product was collected on a filter and washed on the filter with water. The washed product was dewatered by stirring with 99.5 percent of ethanol for 20 minutes and dried in vacuo at 60° C. for 24 hours. 0.7 g of white particles containing 4.6 percent (w/w) Mn was obtained. W$_r$ 8. SRRE 0.01 s$^{-1}$mM$^{-1}$. D$_{av}$ 120 μm.

EXAMPLE 23

1.5 g of carboxymethylated starch gel beads (Example 21) were suspended and swelled in 75 ml distilled water. The pH-value was 6.3. A solution of 0.82 g CuSO$_4$.5H$_2$O in 25 ml distilled water was added, the pH-value was adjusted to 5.5 and the suspension was stirred for 30 minutes. The particles were collected on a filter, washed thoroughly on the filter with distilled water and dried in vacuo at 50° C. 0.8 g of blue green particles containing 6.3 percent (w/w) Cu were obtained. W$_r$ 25. SRRE 0.3 s$^{-1}$ mM$^{-1}$. D$_{av}$ 175 μm. Replacement of CuSO$_4$.5H$_2$O with 1.23 g GdCl$_3$.6H$_2$O gave 0.8 g of white particles containing 10.6 percent (w/w) Gd. W$_r$ 5.6. SRRE 0.1 s$^{-1}$ mM$^{-1}$. D$_{av}$ 85 μm.

EXAMPLE 24

1.5 g of carboxymethyldextran gel beads (CM—Sephadex, C 25, available from Pharmacia Fine Chemicals AB, Uppsala, Sweden—Sephadex is a registered Trade Mark) containing 4.5 milliequivalents of carboxylate groups per g dry substance were swelled in 100 ml distilled water. The pH-value was adjusted to 6.0 and a solution of 2.76 g GdCl$_3$.6H$_2$O in 30 ml distilled water was added during agitation. The pH-value was adjusted to 5.5 and the particles were agitated for 30 minutes. The particles were collected on a filter, washed thoroughly on the filter with 0.9 percent (w/v) NaCl followed by distilled water. The particles were dried in vacuo at 50° C. 0.8 g of white particles containing 18.3 percent (w/w) Gd was obtained. W$_r$ 15.6. SRRE 0.1 s$^{-1}$ mM$^{-1}$. D 100-300 μm. Replacement of CM -Sephadex, C 25 with 1.5 g of carboxymethyldextran gel beads (CM—Sephadex, C 50, available from Pharmacia Fine Chemicals AB, Uppsala, Sweden) containing 4.5 milliequivalents of carboxylate groups per g dry substance and replacement of GdCl$_3$.6H$_2$O with 1.98 g CrCl$_3$.6H$_2$O gave 0.8 g black particles containing 0.14 percent (w/w) Cr. W$_r$ 3.8. SRRE 1.0 s$^{-1}$mM$^{-1}$. D 60-200 μm.

EXAMPLE 25

2.0 g of dextran gel beads (Sephadex G 50, available from Pharmacia Fine Chemicals AB, Uppsala, Sweden) were swelled in 150 ml distilled water. 0.43 ml of epichlorohydrin and 1.0 ml of triethylamine were added and the suspension was shaken for 24 hours at ambient temperature. The particles were collected on a filter, washed on the filter with distilled water and resuspended in 150 ml distilled water. 3.0 g of polyethyleneamine (Polymin SN, available from Badische Anilin- & Sodafabrik, Ludwigshafen, Federal Republic of Germany—Polymin is a registered Trade Mark) were added and the suspension was shaken for 24 hours at ambient temperature. The particles were collected on a filter, washed on the filter with distilled water and resuspended in 150 ml distilled water. 3.4 g of bromoacetic acid were added, the pH-value was adjusted to 9.5 and the suspension was shaken for 24 hours. The particles were collected on a filter, washed on the filter with distilled water, resuspended in 100 ml distilled water and the pH-value was adjusted to 6.3. A solution of 0.75 g $GdCl_3.6H_2O$ in 20 ml distilled water was added and the suspension was shaken for 30 minutes at ambient temperature. The particles were collected on a filter, washed thoroughly with distilled water and dried in vacuo at 50° C. 1.7 g of white particles containing 1.3 percent (w/w) Gd were obtained. $W_r$ 15.6. SRRE 0.32 $s^{-1} mM^{-1}$. D 25-100 μm.

EXAMPLE 26

2 g of cross-linked thiolhydroxypropyl gel beads [prepared from cross-linked dextran gel beads (Sephadex, G 50, available from Pharmacia Fine Chemicals AB, Uppsala, Sweden) by the method described for thiolhydroxypropylagarose gel beads in Acta Chem. Scand. B 29 (1975) 471-4 by R. Axen, H. Drevin and J. Carlsson] having $D_{av}$ 63 μm and a thiol group content of 106 μmol/g were swelled in 50 ml dimethylsulphoxide. After centrifugation 30 ml of dimethylsulphoxide were added. 0.52 g of the bisanhydride of ethylenediaminetetraacetic acid (EDTA), prepared as for the DTPA anhydride in Example 2, were added and the mixture was shaken at ambient temperature for 24 hours. The particles were isolated by centrifugation and 50 ml of distilled water were added. After some time to allow for hydrolysis of unreacted EDTA-anhydride the particles were washed 6 times with water.

0.13 g of $CuSO_4.5H_2O$ in 30 ml distilled water was added and the pH-value was adjusted to 5.0. The particles were isolated by centrifugation and washed with 0.9 percent (w/v) NaCl followed by distilled water. 1.18 g of light blue particles containing 1.7 percent (w/w) Cu were obtained. $W_r$ 8.3. SRRE 0.5 $s^{-1} mM^{-1}$. $D_{av}$ 65 μm.

EXAMPLE 27

To 11 ml of a suspension of carboxymethylated agarose gel beads containing 12 mequivalents carboxylate groups per 100 ml suspension (CM—Sepharose CL 6B, available from Pharmacia Fine Chemicals AB, Uppsala, Sweden—Sepharose is a registered Trade Mark) were added 100 ml distilled water and the pH-value was adjusted to 5.0. 0.36 g of $FeCl_3.6H_2O$ in 20 ml distilled water was added and the pH-value was adjusted to 4.5. The mixture was stirred for 30 minutes. The particles were isolated by centrifugation and washed with 0.9 percent (w/v) NaCl followed by distilled water. 0.37 g of brown particles containing 5.8 percent (w/w) Fe was obtained. $W_r$ 11.3. SRRE 0.1 $s^{-1} mM^{-1}$. D 45-165 μm.

EXAMPLE 28

2 g of cross-linked thiolhydroxypropyl agarose gel beads where the thiol group is protected by 2-thiopyridyl groups [Agarose-$OCH_2CH(OH)CH_2AS$-pyridine (Thiopropylsepharose 6B, available from Pharmacia Fine Chemicals, Uppsala, Sweden—Thiopropylsepharose is a registered Trade Mark)], was converted (activated) to the thiol form, Agarose-$OCH_2CH(OH)CH_2SH$, according to the method described in "Affinity Chromatography, principles and methods", Pharmacia Fine Chemicals, Uppsala, Sweden 1979, p. 43. The activated particles were washed with dry dimethylsulphoxide and suspended in 30 ml of dimethyl sulphoxide. 0.72 g of the bisanhydride of DTPA was added and the mixture shaken for 16 hours. The particles were isolated by centrifugation and 50 ml of distilled water were added. After washing with water 6 times the particles were suspended in 100 ml of distilled water and the pH-value was adjusted to 4.3.

0.11 g of $FeCl_3.6H_2O$ in 25 ml distilled water was added, the ph-value was adjusted to 4 and the mixture was stirred for 20 minutes. The particles were washed with 0.9 percent (w/v) NaCl and distilled water. 1.4 g of brown particles containing 4.8 percent (w/w) Fe were obtained. $W_r$ 10.5. SRRE 0.1 $s^{-1} mM^{-1}$. D 45-165 μm.

EXAMPLE 29

To 3 ml of a suspension of Agarose—$OCH_2CH(OH)CH_2O$—$(CH_2)_4$—$OCH_2CH(OH)CH_2N(CH_2COOH)_2$ gel beads (Chelating Sepharose 6B, available from Pharmacia Fine Chemicals AB, Uppsala, Sweden) mixed with 10 ml of phosphate buffer, pH 5.8, was added 0.40 g $MnCl_2.4H_2O$ in 10 ml phosphate buffer, pH 5.8, and the mixture was shaken for 1.5 h at pH 5.1. The particles were collected on a filter, washed thoroughly with distilled water and dried in vacuo at 50° C. 0.1 g of white particles containing 4.5 percent (w/w) Mn was obtained. The particles swell in water. On suspending 30 mg of the particles in 5 ml glycerol:water (1:2.13)(v:v), $T_1$ was reduced from 1926 ms to 567 ms (37° C., 10 MHz). $D_{av}$ 40 μm.

EXAMPLE 30

35 ml of a suspension of Agarose—$OCH_2CH(OH)CH_2O$—$(CH_2)_4$—$OCH_2CH(OH)CH_2N(CH_2COOH)_2$ gel beads (Chelating Sepharose 6B from Pharmacia Fine Chemicals AB, Uppsala, Sweden) were diluted with 100 ml distilled water. The pH-value was adjusted to 4.5 and a solution of 0.3 g $GdCl_3.6H_2O$ in 20 ml distilled water was added. The pH-value was adjusted to 5.0 and the suspension was shaken for 30 minutes. The particles were collected on a filter, washed thoroughly with distilled water and dried in vacuo at 50° C. 1.7 g of white particles containing 5.5 percent (w/w) Gd were obtained. $W_r$ 15.6. SRRE 0.3 $s^{-1} mM^{-1}$. $D_{av}$ 40 μm.

EXAMPLE 31

2.0 g of cellulose particles (Sigmacell type 20, available from Sigma Chemical Company, St. Louis, U.S.A.—Sigmacell is a registered Trade mark) were suspended in 100 ml of distilled water. 0.43 ml epichlorohydrin and 1.0 ml triethylamine were added and the suspension was shaken for 24 hours at ambient temperature. The particles were collected on a filter, washed on the filter with distilled water and resuspended in 100 ml of distilled water. 3.0 g of diethylenetriamine were added and the suspension was shaken for 24 hours at ambient temperature. The particles were collected on a filter, washed on the filter with distilled water and resuspended in 100 ml of distilled water. 3.4 g bromoacetic acid were added, the pH-value adjusted to 9.5 and the suspension shaken for 24 hours. The particles were collected on a filter, washed on the filter with distilled water, resuspended in 100 ml distilled water and the pH-value was adjusted to 6.2. A solution of 0.3 g $FeCl_3.6H_2O$ in 20 ml distilled water was added, the pH-value was adjusted to 5.3 and the suspension was shaken for 3 hours at ambient temperature. The particles were collected on a filter, washed thoroughly with distilled water and dried in vacuo at 50° C. 1.0 g of brown particles containing 1.0 percent (w/w) Fe was obtained. $W_r$ 4.2. SRRE 0.21 $s^{-1}mM^{-1}$. $D_{av}$ 30 μm.

EXAMPLE 32

1,4,7,10-Tetraazacyclododecane-N,N',N'',N'''-tetraacetic acid (DOTA) was prepared according to the method described in Inorg. Chem. 19 (1980) 1319 by J. F. Desreux, and was reacted with glycine benzylester according to the mixed anhydride method described in Biochem. Biophys. Res. Comm. 77 (1977) 581, or the carbodiimide method described in Example 14 as follows: 12.8 g DOTA in dried DMSO was carefully added to a solution of 6.7 g N-(3-dimethylaminopropyl)-N'-ethyl-carbodiimide hydrochloride and 400 mg N,N-4-dimethylaminopyridine in DMSO. After 30 minutes a solution of 10.6 g of glycine benzylester-p-toluenesulphonate and 3.21 g of N-methylmorpholine was added dropwise during 1 hour. The solution was stirred for 22 hours and lyophilized. The residue was dissolved in water and washed several times with chloroform at pH 2 and 10. The resulting water solution was evaporated and the crude product washed with ethanol/water.

1.0 g DOTA-glycine-benzylester was dissolved in distilled water, to it were added 670 mg $GdCl_3$ and the mixture was warmed to 80° C. with stirring. The pH was adjusted to between 10 and 11 with NaOH and stirring was continued for 1 hour. After cooling of the unclear solution, the pH was adjusted to 5-6 and the solution became clear. The solvent was evaporated and the residue taken up in dry DMSO. The product was bound to 2.0 g of starch gel beads (Example 1, type B) in the way described in Example 14. The particles were purified and isolated as described in Example 2. The particles swell in water. 1.5 g of white particles containing 2.3 percent (w/w) Gd were obtained. $W_r$ 8.7. SRRE 2.0 $s^{-1}mM^{-1}$. $D_{av}$ 1.1.μm. $T_{\frac{1}{2}}$ 10 hrs.

EXAMPLE 33

0.50 g of starch microspheres (Example 1, type E) was suspended and swelled in distilled water. 25 ml of a 0.48 percent (w/v) aqueous solution of $KMnO_4$ were added slowly with stirring at 60° C. The mixture was stirred for 0.5 h and was left standing overnight. By contact with the carbohydrate $KMnO_4$ was reduced to a highly dispersed insoluble form of the Mn (IV) oxidation state entrapped in the microspheres and the partial oxidation of the carbohydrate increased the swelling. The particles were separated by centrifugation, washed with distilled water, de-watered with ethanol and dried at 60° C. in vacuo for 36 hours. 0.46 g of particles containing 7.5 percent (w/w) Mn was obtained. $W_r$ 14.2.

The particles were degradable by amylase. $D_{av}$ 14±8 μm.

Specific relaxation rate enhancement (SRRE) was measured in a NMR proton spin analyzer (RADX Corp., Houston Tex., U.S.A.) at 10 MHz in glycerol:water (1:2.13)(v/v) at 37° C.: 0.012 $s^{-1}$ $mM^{-1}$.

EXAMPLE 34

1.0 g of dry starch gel beads (Example 1, type D) was swelled for 2 hours with a solution of 0.12 g dimercaptosuccinic acid with a pH-value of 6.5 and dried thereafter. The dry starch gel beads were swelled for 2 hours with a solution of 0.51 g $GdCl_3.6H_2O$ in 14 ml distilled water. The particles were washed thoroughly with distilled water and dried in vacuo at 50° C. 1.3 g white particles containing 9.8 percent (w/w) Gd were obtained. $W_r$ 4.6. SRRE 15.4 $s^{-1}$ $mM^{-1}$. $D_{av}$ 1.3.μm.

EXAMPLE 35

1.0 g of dextran gel beads (Sephadex G 50, available from Pharmacia Fine Chemicals AB, Uppsala, Sweden) was swelled for 2 hours with a solution of 0.5 g $GdCl_3.6H_2O$ in 8 ml distilled water at a pH-value of 5.5 and dried thereafter. The dry dextran gel particles were swelled for 2 hours with a solution of 0.48 g $Na_2HPO_4.12H_2O$ in 8 ml distilled water. The particles were washed thoroughly with distilled water and dried in vacuo at 50° C. 1.6 g of white particles containing 2.0 percent (w/w) Gd were obtained. $W_r$ 4.6. SRRE 9.6 $s^{-1}mM^{-1}$. D 35-130 μm.

EXAMPLE 36

2.0 g of carboxymethyl dextran gel beads (CM Sephadex C 25, available from Pharmacia Fine Chemicals AB, Uppsala, Sweden) were swelled for 2 hours with a solution of 1.2 g $FeCl_3.6H_2O$ in 6 ml distilled water at a pH-value of 6 and were dried thereafter. The dry dextran gel beads were swelled for 2 hours with 8 ml of 5M NaOH. The particles were washed thoroughly with distilled water and dried in vacuo at 50° C. 1.5 g of white particles containing 11 percent (w/w) Fe were obtained. $W_r$ 9.2. SRRE 0.2 $s^{-1}mM^{-1}$. D 40-160 μm.

EXAMPLE 37

0.50 g of gadolinium (III) phosphate dextran gel beads was prepared in accordance with Example 35 and suspended in 10 ml of an aqueous solution of 0.9 percent (w/v) NaCl. The suspension was filled in a 10 ml vial and sterilized. The suspension contained 1.0 mg Gd/ml.

EXAMPLE 38

0.328 g of gadolinium (III) DTPA—starch gel beads was prepared in accordance with Example 13 and suspended in 10 ml of 0.9 percent of a sterile aqueous solution of NaCl. The suspension was filled in a 10 ml vial. The preparation was done aseptically. The isotonic suspension contained 4 mg Gd/ml.

EXAMPLE 39

0.37 g of gadolinium (III) starch gel beads was prepared in accordance with Example 17 and suspended in 10 ml of 0.9 percent of an aqueous solution of NaCl. The suspension was filled in a 10 ml vial and sterilized. The suspension contains 1 mg Gd/ml.

EXAMPLE 40

1.0 g of iron (III)—cellulose particles was prepared in accordance with Example 31 and suspended in 100 ml of distilled water containing 50 g of liquid sorbitol, a preserving agent q.s. and a colouring agent q. s.

The suspension was filled in a 100 ml bottle. The suspension contained 0.1 mg Fe/ml.

EXAMPLE 41

The following powder was mixed: 0.77 g of gadolinium (III)—dextran gel beads prepared in accordance with Example 25, 5 g of saccharose and colouring agent q.s. The powder was filled in a 100 ml bottle. When adding 100 ml of water the suspension contains finally 0.1 mg of Gd/ml.

We claim:

1. A method of diagnosis which method comprises administering to a human or a non-human animal body or to a selected region thereof a contrast effective amount of a diagnostic agent comprising a physiologically tolerable, water insoluble, water-swellable, hydroxyl group containing, particulate macromolecular product which is cross-linked to form a three-dimensional network and carries within cavities therein at least one non-radioactive paramagnetic metal species, said product comprising at least one water-insoluble material selected from the group consisting of polysaccharides, polymerized sugar alcohols and derivatives thereof; and generating an NMR or ultrasound image of said region.

2. A method of diagnosis which method comprises administering to a human or non-human animal body or to a selected region thereof a constant effective amount of a diagnostic agent comprising a physiologically tolerable, water insoluble, water-swellable, hydroxyl group containing macromolecular product comprising particles of a water-insoluble macromolecular material selected from the group consisting of starch, dextrin and derivatives thereof which particles carry in cavities therein at least one non-radioactive paramagnetic metal species, said particles in aqueous media having particle sizes in the range of 6–200 micrometers, and generating an NMR or ultrasound image of said region.

3. A method according to claim 1 wherein said macromolecular product is administered suspended in a physiologically acceptable aqueous liquid.

4. A method according to claim 3 wherein said macromolecular product is administered together with a viscosity enhancing agent.

5. A method according to claim 3 wherein said macromolecular product is administered together with an osmolality regulator.

6. A method according to claim 2 wherein said non-radioactive paramagnetic metal is selected from the group consisting of elements having atomic numbers 21–29, 42, 44 and 57–70.

7. A method according to claim 6 wherein said non-radioactive paramagnetic metal is selected from the group consisting of gadolinium, erbium, europium, dysprosium, holmium, manganese, iron, nickel, chromium and copper.

8. A method according to claim 7 wherein said paramagnetic metal is gadolinium.

9. A method according to claim 1 wherein said non-radioactive metal species is in a water-insoluble or sparingly soluble substance at least partially filling said cavities in said macromolecular product.

10. A method according to claim 1 wherein said macromolecular product is in the form of water swellable particles which in their water-swollen state contain 10–98 percent by weight of water.

11. A method according to claim 1 wherein said macromolecular product is in the form of water swellable particles which in their water-swollen state have a particle size within the range 0.01–1000 μm.

12. A method according to claim 1 wherein said macromolecular product is material degradable in the animal body.

13. A method according to claim 12 wherein said macromolecular product is a material enzymatically degradable by hydrolases.

14. A method according to claim 1 wherein said non-radioactive paramagnetic metal is selected from the group consisting of elements having atomic numbers 21–29, 42, 44 and 57–70.

15. A method according to claim 14 wherein said non-radioactive paramagnetic metal is selected from the group consisting of gadolinium, erbium, europium, dysprosium, holmium, manganese, iron, nickel, chromium and copper.

16. A method according to claim 1 wherein said macromolecular product comprises a polysaccharide material or a derivative thereof.

17. A method according to claim 1 wherein said macromolecular product comprises a material selected from starches, dextrans and derivatives thereof.

18. A method according to claim 1 wherein said macromolecular product comprises a cellulose or a derivative thereof.

19. A method according to claim 12 wherein said macromolecular product is a material degradable by alpha-amylase.

20. A method according to claim 1 wherein said macromolecular product has a particle size of 0.1 to 3 microns when in aqueous media.

21. A method according to claim wherein said paramagnetic metal is gadolinium.

22. A method according to claim 1 the particles whereof have no electrical charge when in aqueous suspension.

* * * * *